(12) United States Patent
Salihoglu et al.

(10) Patent No.: US 11,235,095 B2
(45) Date of Patent: Feb. 1, 2022

(54) FEMORAL ARTERIAL ECMO (EXTRACORPOREAL MEMBRANE OXYGENATION) CANNULA

(71) Applicants: T.C ISTANBUL MEDIPOL ÜNIVERSITESI, Istanbul (TR); T.C ISTANBUL ÜNIVERSITESI, Istanbul (TR)

(72) Inventors: Ece Salihoglu, Istanbul (TR); Ziya Salihoglu, Istanbul (TR); Yahya Yildiz, Istanbul (TR); Ugur Ozgur Yildiz, Istanbul (TR)

( * ) Notice: Subject to any disclaimer, the term of this patent is extended or adjusted under 35 U.S.C. 154(b) by 282 days.

(21) Appl. No.: 16/492,688

(22) PCT Filed: Mar. 16, 2018

(86) PCT No.: PCT/TR2018/050100
§ 371 (c)(1),
(2) Date: Sep. 10, 2019

(87) PCT Pub. No.: WO2018/169503
PCT Pub. Date: Sep. 20, 2018

(65) Prior Publication Data
US 2020/0046892 A1    Feb. 13, 2020

(30) Foreign Application Priority Data
Mar. 17, 2017  (TR) ................. 2017/04099

(51) Int. Cl.
| A61M 1/36  | (2006.01) |
| A61B 17/00 | (2006.01) |
| A61B 17/34 | (2006.01) |
| A61M 25/10 | (2013.01) |
| A61B 17/22 | (2006.01) |

(52) U.S. Cl.
CPC ..... *A61M 1/3659* (2014.02); *A61B 17/00234* (2013.01); *A61B 17/3421* (2013.01); *A61M 25/10* (2013.01); *A61B 2017/22051* (2013.01); *A61B 2017/3486* (2013.01)

(58) Field of Classification Search
CPC . A61B 2017/22051; A61B 2017/3486; A61M 1/3653; A61M 1/3659; A61M 2025/1095; A61M 25/005; A61M 25/10; A61M 60/857
See application file for complete search history.

(56) References Cited

U.S. PATENT DOCUMENTS

| 8,986,283 B2* | 3/2015 | Rajendran ......... A61M 5/14244 604/512 |
| 2008/0294102 A1* | 11/2008 | Cartledge ............. A61M 25/10 604/103.01 |

* cited by examiner

*Primary Examiner* — Deanna K Hall
(74) *Attorney, Agent, or Firm* — Egbert, McDaniel & Swartz, PLLC

(57) ABSTRACT

A femoral arterial ECMO cannula is provided with a balloon that has dual flow and which provides arterial body blood flow during femoral ECMO (Extra Corporeal Membrane Oxygenation).

23 Claims, 3 Drawing Sheets

FEMORAL ARTERIAL ECMO (EXTRACORPOREAL MEMBRANE OXYGENATION) CANNULA

TECHNICAL FIELD

Figure 1:
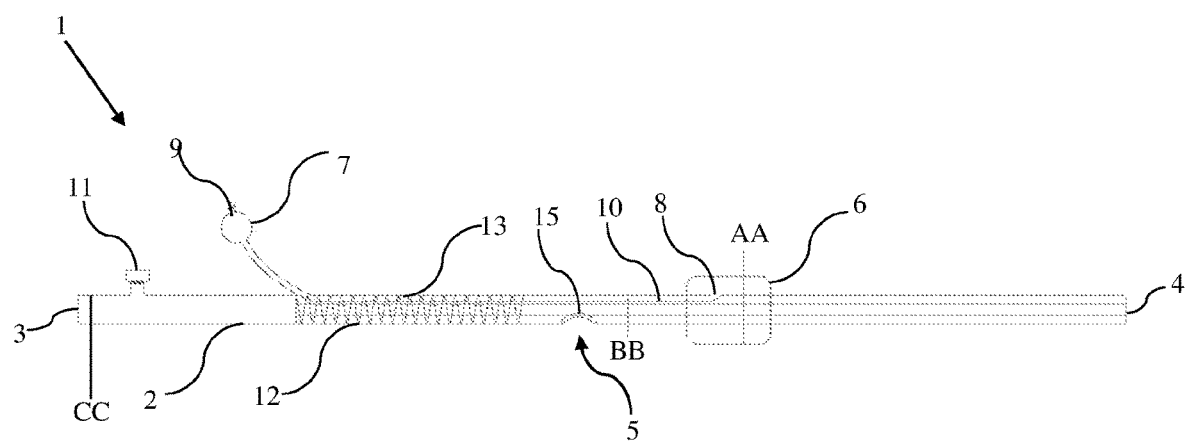

The present invention is related to a balloon femoral arterial ECMO cannula that has dual flow and that provides arterial body blood flow during femoral ECMO (ExtraCorporeal Membrane Oxygenation).

PRIOR ART

Extracorporeal Membrane Oxygenation (ECMO) is a method used in patients with heart or respiratory failure in all age groups who do not respond to traditional treatment modalities. With the ECMO system, cannula or cannulas are used to remove dirty (venous) blood, and after the oxygenation of the blood is established, the arterial blood is re-injected. For this purpose, the femoral artery (the main artery of the leg) is frequently used to provide arterial blood flow, especially in older children and adults.

Currently, in the ECMO applications femoral arterial cannulas adversely affect the blood flow of the leg and lead to serious problems such as finger or foot loss, skin loss, infection due to nutrition problems. In order to overcome problems different solutions are used. The first one is to place a cannula that is smaller than needed into the femoral artery. In this solution, it becomes difficult to provide the required body perfusion support and also it is not possible to provide blood flow that guarantees safe blood nourishment to the leg.

In another method, a second cannula is placed at a point that is separate from the location of the main cannula and that will only feed the leg. This method requires a second and technically difficult procedure for the patient and increases the cost with the use of the second cannula, thereby increasing the likelihood of medical problems such as bleeding or infection.

Another method is to form a Y-shaped arm with an artificial vein in the leg vein of the patient and placing a cannula from here. This method requires an important second surgical procedure for the patient and even with the use of this method the risk of malnutrition of lower ends of the leg, such as fingers, cannot be removed completely.

In U.S. Pat. No. 5,001,121, which discloses another method, a second opening is opened into the femoral artery cannula so that the mouth in the end provides body perfusion while the second mouth provides protection of the leg blood flow. However, a simple opening does not guarantee the leg blood flow, since the characteristic of the arteries is that the artery spasms and wraps over the cannula and the second opening, that is on the side may become dysfunctional. Another risk is that it is difficult to make sure that the opening is correctly placed in the leg vein and remains in the proper position. In this case, there is no blood flow when the opening in not placed in the leg vein correctly and the opening is towards the wall U.S. Pat. No. 2012/0259273 in which another solution is mentioned, discloses that in order to protect the second opening and the correct flow through the second opening an elbow can be placed right above the second opening such that it forms a structure like an eaves or a tarpaulin in order to prevent closing of this second opening. However, the presence of the elbow on the second opening increases the diameter of the cannula in that location leads to risk of damaging the vein wall while placing the cannula and also while removing the cannula. Additionally, the direction of the elbow leads to risk of permanent risk of damaging the vein wall while removing the cannula.

When a cannula having a second opening is used, in order to secure the blood flow through said opening, it is necessary to form an angled barrier into the opening region of the cannula. In said design, there is a second lumen in the cannula. In both applications, passage of the blood from a narrow region with high speed and crashing into the barrier leads to damaging of the blood elements and pose the risk of a general tendency to cause general bleeding in the body.

Currently, balloon perfusion catheters are used. However, just like the area of use is different, the purpose of use and the placement location of the balloon are also different.

As an example of this kind of use, it is possible to mention the catheters that are placed into the aorta and used for coronary artery feeding.

In another design, a Y or T shaped femoral cannula design is suggested. However, this design is not user-friendly and involves technical difficulties when placing and removing.

The document numbered TR 2011/07038 discloses a system that is directed to preventing loss of limb in situations like ischemia, gangrene or requiring amputation where the distal veins are blocked and collateral circulation is insufficient. In said invention, with the help of the inflatable balloon located in the middle of the catheter, a pressure difference is formed in the vein and sufficient perfusion is provided in the region where catheter is located.

Korean patent document KR 20160103474 discloses a bi-directional cannula tube system located in a vein in the femoral artery and which helps to provide a stable blood flow. In this regard, with the cannula of that invention it is aimed to reduce the risk of ischemia which may occur during surgery, or to prevent complications that may occur. It is aimed to provide stable bi-directional blood flow with the help of the opening in this cannula. However, the angled structure of the secondary opening causes the risk of vein damage or even vein disintegration when the cannula is removed from the vein after the procedure.

BRIEF DESCRIPTION OF THE INVENTION

The object of the present invention is to realize a femoral arterial ECMO cannula in which a single cannula is used and both the body and the leg that is treated with cannula have a safe and continuous blood flow.

Another object of the invention is to realize a femoral arterial ECMO cannula in situations like ECMO (Extra Corporeal Membrane Oxygenation) where long term body perfusion is necessary or like open heart surgery where short term femoral perfusion is necessary to provide body blood flow and to prevent leg ischemia.

DETAILED DESCRIPTION OF THE INVENTION

"A femoral arterial ECMO cannula" for achieving the object of the present invention is illustrated in the attached figures, wherein;

FIG. 1. The side view of a femoral arterial ECMO cannula according to invention.

Figure 2:
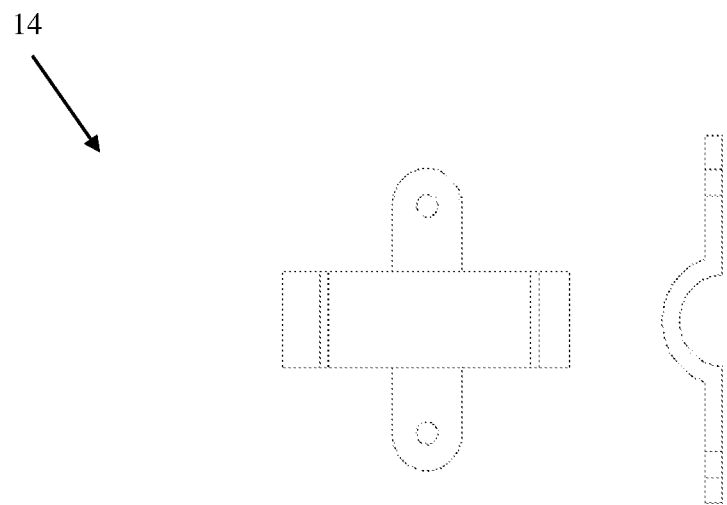

FIG. 2. The top and rear view of the clamp used in the femoral arterial ECMO cannula of the invention.

Figure 3:
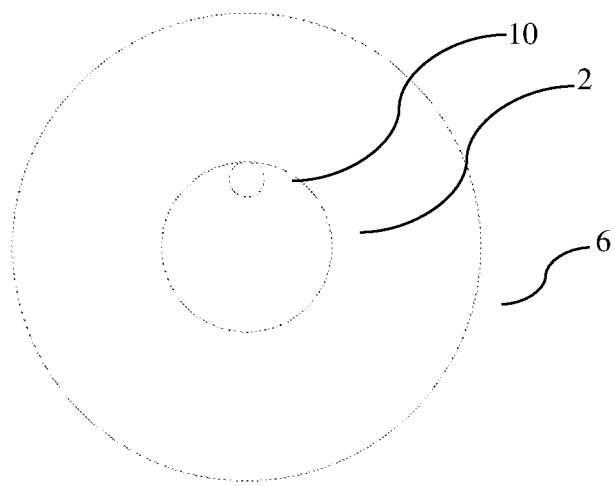

FIG. 3. A view of AA section in FIG. 1

Figure 4:
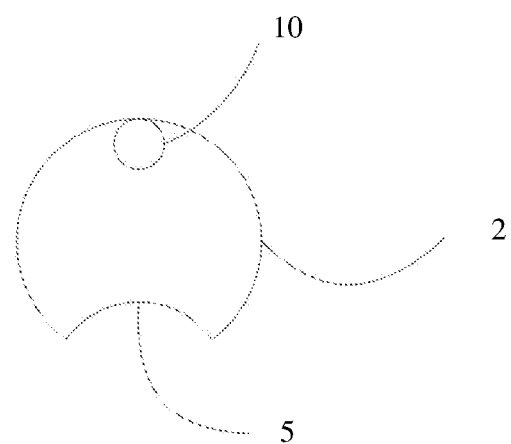

FIG. 4. A view of BB section in FIG. 1

Figure 5:
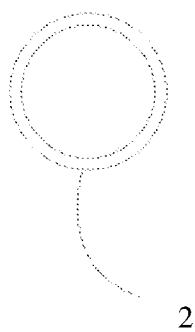

FIG. 5. A view of CC section in FIG. 1

The parts in the figures are numbered individually and their correspondences are given below.
1. Cannula
2. Body
3. Opening
4. Distal feed opening
5. Feed opening
6. Balloon
7. Balloon pilot
8. Inflation opening
9. Two-way valve
10. Balloon inflation path
11. Luer Connection
12. Reinforced area
13. Anti bacterial coating
14. Clamp
15. Indicator The subject of the invention is a femoral arterial ECMO cannula (1) comprising,
- at least one cylindrical shaped body (2) comprising at least one opening (3) that allows for permeation of blood and at which the blood enters from, on the other end a distal feed opening (4) from which the blood leaves to provide feeding, and one feed opening (5) that is located between the two openings (3, 4) used for exit of blood for the purpose of feeding,
- at least one balloon (6) situated between the feed opening (5) and the distal feed opening (4) on the body (2),
- at least one balloon pilot (7) located on the body (2) for inflating the balloon (6) which is connected via at least one balloon inflation opening (8) from one end to the balloon (6) and comprising at least one controlled bidirectional valve (9),
- at least one balloon inflation path (10) located on the body (2) which is connected with a balloon pilot (7) from one end with b the balloon (6) from the other end, providing transfer of the serum to the balloon (6),
- at least one luer connection (11) located on the body (2), preferably close to the opening (3) into which the blood enters,
- at least one reinforced area (12) that is resilient and resistant to breakage and located on the top of the body (2),
- at least one anti-bacterial coating (13) located on the upper part of the body (2) that is in contact with the patient's skin and,
- at least one clamp (14) securing the body (2) on the patient's skin.

In the femoral arterial ECMO cannula (1) of the invention, when the balloon (6) on the body (2) is inflated, it takes the shape of a rectangular prism. In the inflated position, the balloon (6), which is in the form of a rectangular prism, helps to move the vessel wall away from the body (2) thus preventing spasm and closing of the feed opening (5). In addition, with the inflation of the balloon (6) the blood that enters through the feed opening (5) is directed only towards the leg. Additionally, the pressure that will be applied to the vessel walls by the inflated balloon (6) has been equalized according to the elliptical balloons used in the prior art and thus damaging of the vessel with the balloon (6) is prevented.

In the preferred embodiment of the invention, the opening (3) has a round cross-section. The opening (3) permits the incoming blood for perfusion to reach the body from the distal feed opening (4) and preferably to reach leg from the feed opening (5).

In a preferred embodiment of the invention the distal feed opening (4) located at the end of the body (2) and feeding the body has an oval opening that improves blood flow and reduces the friction. Preferably, the distal feed opening (4) is in the shape of a fish mouth. There is a mutual C-shaped holes on the wall of the cylindrical body (2) at the end feed opening (3) for giving the fish mouth shape.

In the cannula (1) of the present invention, the feed opening (5) comprises at least one indicator (15) that is used for determining the direction. The indicator (15) in the feed opening (5) is C-shaped and preferably made of radio opaque material. The feed opening (5) is preferably used for blood passage which provides blood flow to leg. In order to ensure continuous blood supply of the feed opening (5), the balloon (6) must be inflated to contact the vessel wall. In this way, both leg and body perfusions are performed without reverting blood fed to the body from the blood vessels.

In the invention, in balloon (6) in inflated position takes the shape of a rectangular prism and creates that same pressure on every vessel wall in comes in contact with. The balloon (6) starts to inflate via reaching of the serum which forms with induction of the balloon pilot (7) that reach the balloon (6) from the inflation opening (8) through inflation path (10). In a preferred embodiment of the invention there are two more indicators (15) that remain on top and bottom of the balloon (6) on the body (2). By this way, the location of the balloon (6) in the vessel can be controlled. The markers located at the top and bottom of the balloon (6) will wrap around the body (2).

In a preferred embodiment of the invention, the balloon (6) is made from a flexible material. During the placement or removal of the cannula (1) the serum inside the balloon (6) is discharged and the balloon (6) is in deflated state and.

In the femoral arterial ECMO cannula (1) of the present invention, at one end of the balloon pilot (7) there is a controlled bidirectional valve and on the other end there is the balloon inflation path (10) from which the serum is transmitted to the balloon (6). The balloon inflation path (10) transmits serum to the balloon (6) through balloon inflation opening (8). In a preferred embodiment of the invention, the balloon inflation path (10) is concealed in the lumen located in the body (2) from which the blood passes.

In a preferred embodiment of the invention, a luer connection is used to evacuate the serum present at the balloon (6). The luer connection (11) is located at a position close to the end of the body which has the opening (3) The luer connection (11) is in communication with the balloon inflation path (10) in the body (2) and with the opening of the luer the serum inside the balloon is evacuated and the balloon is deflated.

In a preferred embodiment of the invention the reinforced area (12) starts from a point close to the indicator (15) that is located in a close proximity to the feed opening (5) of the balloon (6) and continues until the luer (11) that is at the end of the body (2). In another preferred embodiment of the invention, there is another indicator (15) on the body (2) starting from the end that is close to luer and leads up to distal feed opening (4). The reinforced area (12) is formed on the body (2) with a wire-like material wound on the body (2).

In the present invention, the anti-bacterial coating (13) is preferably made of silver a similar material. The anti-bacterial coating (13) is located between the feed opening (4) located at the upper part of the body (2) and the point at which the balloon inflation path joins the body (2), such that is it in the part of the body (2) that is in contact with patient's skin. With the use of anti-bacterial coating (13), the risk of infecting the patient is reduced in long-term use.

In the cannula (1) of the present invention, the clamp (14) can be attached to and detached from the body (2) and with the help of two ears that are present on the clamp, the clamp can be tied to the skin of the patient (14) with preferably a suture thread. The clamp (11) can be attached to and detached from the cannula (1) body (2) by enlarging with the help of its opening and its elastic structure. Said clamp (14) comprises two channels that help fixing to the skin via winding of the suture thread. In a preferred embodiment of the invention the clamp (14) is located in the region that is between the reinforced area (12) and serum evacuation luer (11) (FIG. 2).

The cannula (1) that is subject of the present invention is implanted by the Seldinger method. After placement of the cannula (1), the balloon (6) is inflated and the vessel wall is removed from the body of the cannula (2). This way, closing of the feed opening due to spasm is prevented and blood flow originating from the feed opening (5) is directed only to the leg. In cases where removal of the cannula (1) after its use is desired, balloon (6) is deflated from the luer connection (11) and the cannula (1) is removed without causing damage to vessel wall. The indicators (15) located on various places on the body (2) are detected by radiography due to its radio opaque property and the location of body (2) and as a result the cannula (1) in the vessel is followed. After the insertion of the cannula (1), while the blood flow through the feed opening (5) is followed with ultrasound, the balloon is inflated (6), and the body is stabilized on the skin with the clamp (14) after making sure that the cannula (1) is placed correctly and the leg blood flow is directly seen.

Around these basic concepts, it is possible to develop a wide variety of applications for the inventive subject "A femoral arterial ECMO cannula (1)" and the invention is not limited to the examples disclosed herein, but is essentially as specified in the claims.

The invention claimed is:
1. A femoral arterial ECMO cannula comprising:
at least one cylindrical body having at least one proximal opening at one end adapted to allow for permeation of blood and to allow the blood to enter thereinto and having a distal opening at an opposite end thereof adapted to allow the blood to exit the at least one cylindrical body, said at least one cylindrical body having at least one feed opening positioned between the at least one proximal opening and the distal opening, the feed opening having at least one indicator;
at least one balloon positioned between the feed opening and the distal opening on said at least one cylindrical body, the feed opening adapted to feed said at least one balloon;
at least one balloon pilot located on said at least one cylindrical body and adapted to inflate said at least one balloon, said at least one balloon pilot being connected to said at least one balloon via at least one balloon inflation opening at one end of said at least one balloon, said at least one balloon pilot having at least one controlled bidirectional valve;
at least one balloon inflation path located on said at least one cylindrical body and connected at one end to said at least one balloon pilot and adapted to allow transfer of serum to said at least one balloon;
at least one luer connection located on said at least one cylindrical body adjacent to the at least one proximal opening;
at least one reinforced area positioned at a top of said at least one cylindrical body, said at least one reinforced area being resilient and breakage-resistant;
at least one anti-bacterial coating located on an upper part of said at least one cylindrical body, said at least one anti-bacterial coating adapted to contact a skin of a patient; and
at least one clamp cooperative with said at least one cylindrical body and adapted to secure said at least one cylindrical body to the skin of the patient, said at least one balloon being prismatically-shaped when inflated.

2. The femoral arterial ECMO cannula of claim 1, wherein the at least one proximal opening has a circular cross-section.

3. The femoral arterial ECMO cannula of claim 1, wherein the distal opening has an oval shape.

4. The femoral arterial ECMO cannula of claim 1, wherein the distal opening has a fish-mouth shape.

5. The femoral arterial ECMO cannula of claim 1, wherein the at least one proximal opening comprises C-shaped holes formed in a wall of said at least one cylindrical body.

6. The femoral arterial ECMO cannula of claim 1, wherein the at least one indicator is C-shaped and is formed of a radiopaque material.

7. The femoral arterial ECMO cannula of claim 1, wherein said at least one balloon pilot is adapted to allow the serum to enter and inflate said at least one balloon, the serum reaching said at least one balloon pilot from the at least one balloon inflation opening through said at least one balloon inflation path.

8. The femoral arterial ECMO cannula of claim 1, wherein the at least one indicator comprises at least two indicators positioned respectively at the top and at the bottom of said at least one balloon.

9. The femoral arterial ECMO cannula of claim 8, wherein the at least two indicators wrap around said at least one cylindrical body.

10. The femoral arterial ECMO cannula of claim 1, wherein said at least one balloon is formed of an elastic material.

11. The femoral arterial ECMO cannula of claim 1, wherein said at least one balloon pilot has the at least one controlled bidirectional valve at one end and said at least one balloon inflation path at an opposite end.

12. The femoral arterial ECMO cannula of claim 1, wherein said at least one balloon inflation path transmits the serum to said at least one balloon through the at least one balloon inflation opening.

13. The femoral arterial ECMO cannula of claim 1, wherein said at least one cylindrical body has a lumen therein, said at least one balloon inflation path being in the lumen.

14. The femoral arterial ECMO cannula of claim 1, wherein said at least one luer connection is in communication with said at least one balloon inflation path, said at least one luer connection being openable so as to allow the serum in said at least one balloon to evacuate therefrom and to allow said at least one balloon to deflate.

15. The femoral arterial ECMO cannula of claim 1, wherein said at least one reinforced area starts from a point adjacent to the at least one indicator and extends to said at least one liter connection.

16. The femoral arterial ECMO cannula of claim 1, wherein the at least one indicator comprises an indicator on said at least one cylindrical body that starts adjacent to said at least one luer connection and extends to the distal opening.

17. The femoral arterial ECMO cannula of claim 1, wherein said at least one reinforced area is a wire material wound on said at least one cylindrical body.

18. The femoral arterial ECMO cannula of claim 1, wherein said at least one anti-bacterial coating is formed of a silver material.

19. The femoral arterial ECMO cannula of claim 1, wherein said at least one anti-bacterial coating is located between the distal opening of said at least one cylindrical body and a point at which said at least one balloon inflation path joins with said at least one cylindrical body.

20. The femoral arterial ECMO cannula of claim 1, wherein said at least one clamp is detachable from said at least one cylindrical body, said at least one clamp having a pair of ears, said at least one clamp adapted to be tied to the skin of the patient by a suture thread extending from the pair of ears.

21. The femoral arterial ECMO cannula of claim 1, wherein said at least one clamp has an elastic, structure, said at least one clamp having an opening therein that is expandable by virtue of the elastic structure so as to allow said at least one clamp to be attached to and detached from said at least one cylindrical body.

22. The femoral arterial ECMO cannula of claim 1, wherein said at least one clamp has a pair of channels thereon.

23. The femoral arterial ECMO cannula of claim 1, wherein said at least one clamp is located in an area between said at least one reinforced area and said at least one leer connection on said at least one cylindrical body.

* * * * *